United States Patent [19]

VanBeek

[11] Patent Number: 5,039,198
[45] Date of Patent: Aug. 13, 1991

[54] STEREOSCOPIC MICROSURGERY SYSTEM

[76] Inventor: Allen L. VanBeek, 7115 Antrim Rd., Edina, Minn. 55439

[21] Appl. No.: 388,394

[22] Filed: Aug. 2, 1989

[51] Int. Cl.⁵ .............................................. G02B 6/06
[52] U.S. Cl. .................................................. 385/117
[58] Field of Search ................ 350/96.25, 96.26, 96.10

[56] References Cited

U.S. PATENT DOCUMENTS

| | | | |
|---|---|---|---|
| 3,609,016 | 9/1971 | Jampolsky | 350/96.25 |
| 3,664,330 | 5/1972 | Deutsch | 350/96.25 |
| 4,695,129 | 9/1987 | Faessen et al. | 350/96.25 |
| 4,735,473 | 4/1988 | Migozzi et al. | 350/96.25 |

Primary Examiner—William L. Sikes
Assistant Examiner—Robert E. Wise
Attorney, Agent, or Firm—Hugh D. Jaeger

[57] ABSTRACT

Stereoscopic microsurgery system for depth of field viewing of a surgical procedure internal in the human body, including a head mounted viewing assembly with dual optics, a retractor, and a bundled fiber optic aspiration or suction tubing therebetween. The head mounted viewing assembly includes dual optical viewers which move longitudinally and laterally in x-y-z planes to adjust to a surgeon's eyesight. Containment tubing between the head mounted viewing assembly and the retractor provides for internally contained fiber optic cables for vision, illumination, as well as aspiration or suction at an internal surgical site. The dual functioning optical viewing assemblies provide for visual stereoscopic depth perception at the internal surgical site by the surgeon. The surgical sites can be for the following procedures:

a. Anthroscopic
b. Laproscopic
c. Gastroscopy
d. Colonoscopy
e. Thorascopy
f. Anocoscopy
g. Esophagoscopy
h. Cystoscopy
i, Choudochoscopy 7 Claims, 6 Drawing Sheets

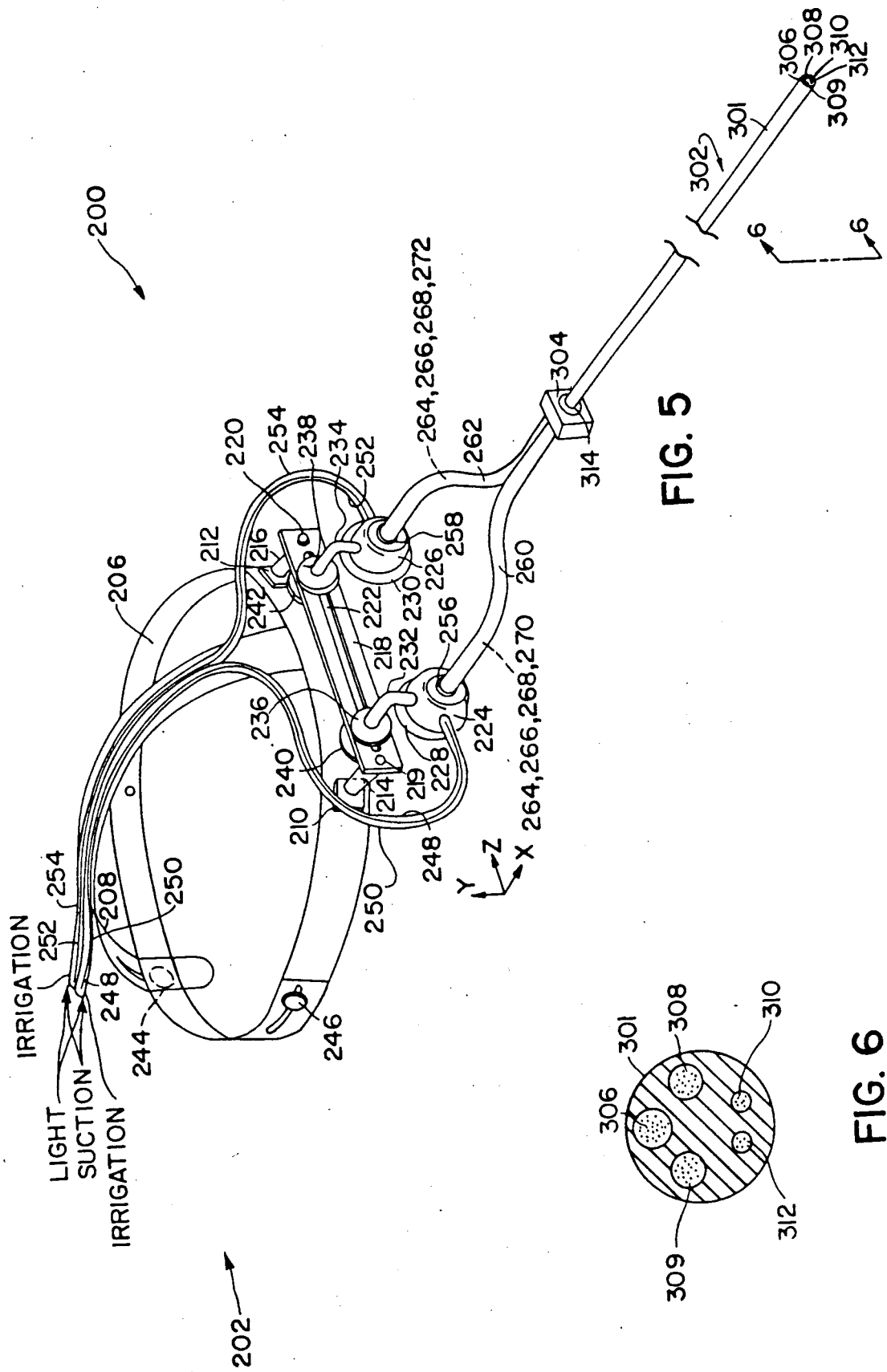

STEREOSCOPIC MICROSURGERY SYSTEM

BACKGROUND OF THE INVENTION

1. Field of the Invention

The present invention pertains to surgical instrumentation, and more particularly, pertains to a stereoscopic microsurgery system which provides for depth of field viewing of a remote surgical site in a human body, such as in the thoracic cavity.

2. Description of the Prior Art

Prior art viewing systems have been limited to a single fiber optic bundle, requiring manual dexterity to hold the viewing scope at the surgeon's or doctor's eye, as well as positioning the viewing scope within a human body cavity. Except to the most highly skilled surgeon, this has been awkward and cumbersome task. The prior art viewing systems also did not provide for a depth of field viewing because of the single viewing optic and the natural optical characteristics of the surgeon's eyes. It has been nearly impossible to obtain any depth of field viewing.

The present invention overcomes the deficiencies of the prior art by providing a stereoscopic microsurgery system for viewing with depth of field of a surgical site in the human body such as in the thoracic cavity.

SUMMARY OF THE INVENTION

The general purpose of the present invention is to provide a stereoscopic microsurgery system which provides depth of field viewing for the surgeon. Two fiber optic bundles positioned on a microsurgery paddle extend from the end of the paddle at the operating site to the optics which are positioned in front of the surgeon's eyes. There is a separation of the fiber optic bundles, as well as the optics of the surgeon's eyes, to provide for the necessary depth of field viewing.

According to one embodiment of the present invention, there is provided a retractor with a paddle and a handle, fiber optics positioned about the paddle, the fiber optics of a length so that the paddle can be positioned in a cavity of the human body and also provide flexibility in the cable. The fiber optics connect to optic assemblies, and the optic assemblies are moveable in an x-y-z plane and are positioned on a suitable head bracket. The cable bundles can include a fiber optic light bundle, the viewing optic bundle, a suction tube, and an aspiration tube. Appropriate lenses can be provided at either end of the optic bundle for proper optical and viewing configurations. The optic bundles can also be separate and distinct from the suction and aspiration tubes. The optical viewing assemblies about the surgeon's eyes are movable in an x-y-z direction. The viewing assemblies mount on the headband, and the light and suction tubes position over the surgeon's head on the headband.

Significant aspects and features of the present invention include a stereoscopic viewing system which provides depth of field at a surgical operating site for internal cavities of the body, such as the thoracic cavity by way of example and for purposes of illustration.

Another significant aspect and feature of the present invention includes an assembly which is sterilizable, such as by ETO.

A further significant aspect and feature of the present invention is a paddle which supports the fiber optic viewing and light bundles, the light bundles and the suction tubes which are of such a size as to fit in through a small slit in the body, such as 1-3 cm for microsurgery procedures, such as for breast implants by way of example and for purposes of illustration.

Having thus described the embodiments of the present invention, it is the principal object hereof to provide a microscopic surgery system including a plurality of viewing optics through fiber optic bundles which provide depth of field for viewing of a surgical site in the human body.

One object of the present invention is to provide a stereoscopic microsurgery system for viewing of a surgical site with two fiber optic tubes supported on a paddle. The paddle is manipulated by the surgeon's hands.

Another object of the present invention is to provide an assembly which is sterilizable and includes disposable suction and aspiration tubes. The remaining assembly of the headband, the optics, the fiber optic tubes and the retractor are sterilizable such as with an ETO gas process.

Still another object of the present invention is the optics of a viewing system which are adjustable in an x-y-z direction with respect to the surgeon's eyes.

Another object of the present invention is to provide a stereoscopic microsurgery system for viewing of a surgical site with a single fiber optic tube supported on a retractor.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 5 illustrates a second alternative embodiment of the stereoscopic microsurgery system;

FIG. 6 illustrates a cross-sectional view taken along line 6—6 of FIG. 5; and,

DESCRIPTION OF THE PREFERRED EMBODIMENTS

Figure 1:
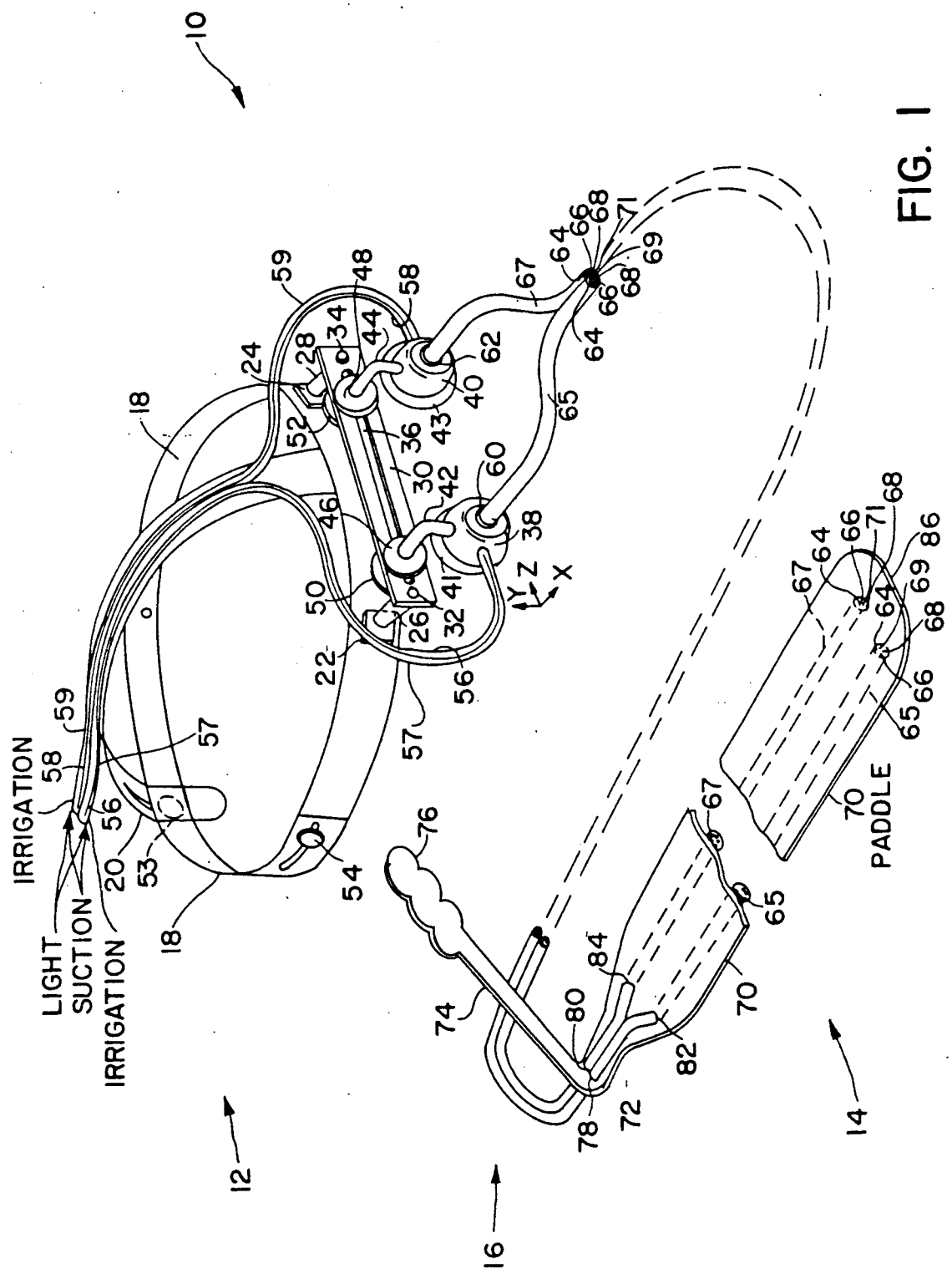
FIG. 1 illustrates a perspective view of a stereoscopic microsurgery system.
Figure 2:
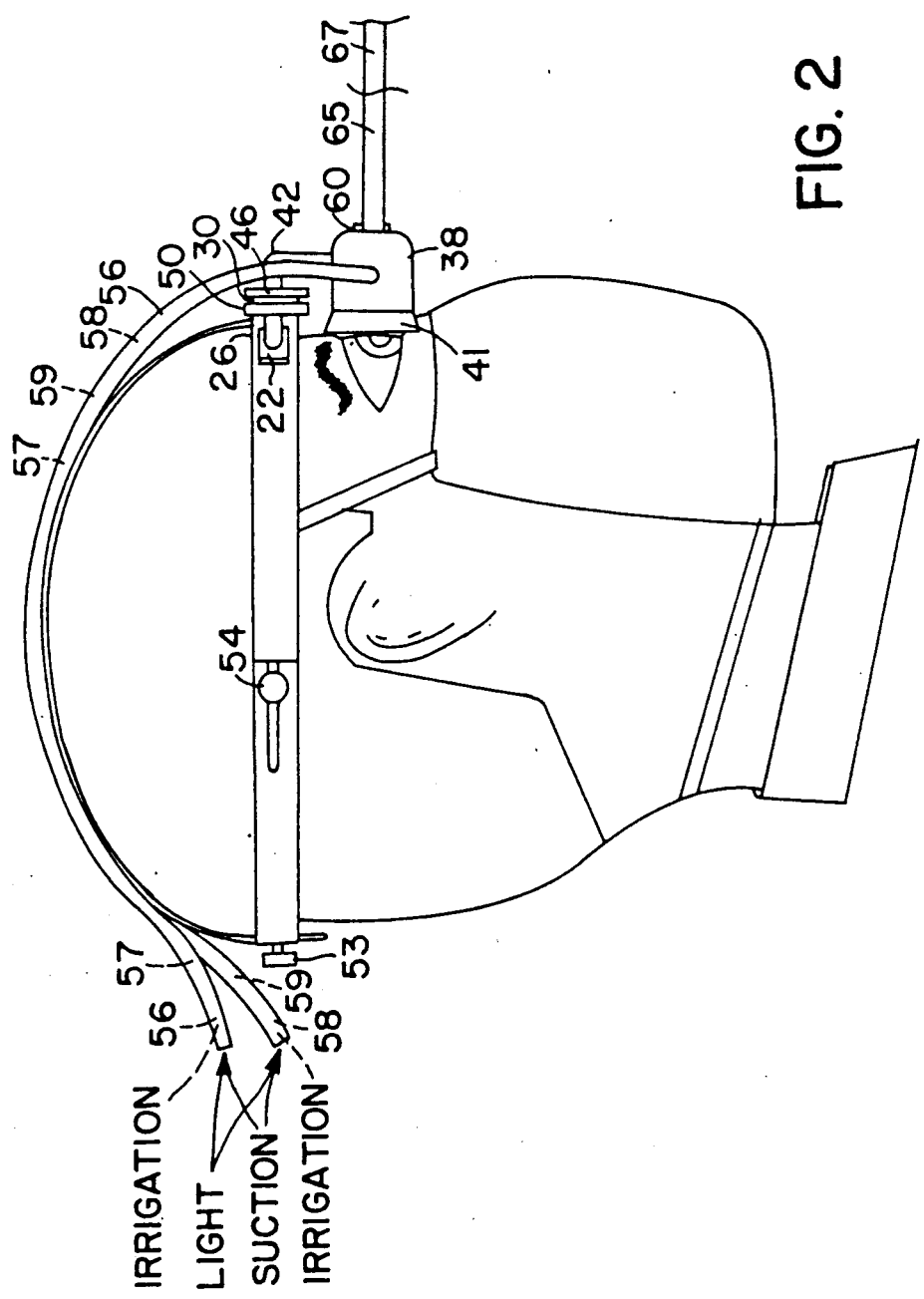
FIG. 2 illustrates a side view of the stereoscopic microsurgery system mounted viewing assembly.

FIG. 1 illustrates a perspective view of a stereoscopic microsurgery system 10 including a head mounted viewing assembly 12, a retractor 14 and bundled fiber optic tubing 16 between the head mounted viewing assembly 12 and the retractor 14. The head mounted viewing assembly 12 includes a horizontally aligned adjustable circular headband 18, an adjustable vertically aligned strap member 20 extending from the front of the circular headband 18 to the rear of the circular headband 18, mounting blocks 22 and 24 secured to the circular headband 18, mounting posts 26 and 28 secured to and extending horizontally from the mounting blocks 22 and 24, respectively, a horizontally aligned adjustment plate 30 secured to the mounting posts 26 and 28 by machine screws 32 and 34, and an adjustment slot 36 extending horizontally through the adjustment plate 30. Also included in the head mounted viewing assembly 12 are adjustable optical viewers 38 and 40, rubber ring gaskets 41 and 43 about the aft edge of the adjustable optical viewers 38 and 40, respectively, and appropriate mounting hardware including threaded angled brackets 42 and 44 extending vertically from the adjustable optical viewers 38 and 40 and further extending horizontally through the adjustment slot 36. Threaded adjustment knobs 46 and 48 secure over the threaded angle brackets 42 and 4 in the adjustment slot 36 to locate and tighten against the adjustment plate 30. Opposing threaded lateral adjustment knobs 50 and 52 also engage the threaded horizontal ends of the threaded angle brackets 42 and 44, and are tightened individually against the adjustment plate 30, forcing the threaded adjustment knobs 46 and 48 against the adjustment plate 30 to provide securement and independent lateral longitudinal and pivotal adjustment of the adjustable optical viewers 38 and 40 so that a surgeon may properly space the optical viewers about his individual eyes. Vertical positioning of the adjustable optical viewers 38 and 40 is accomplished by adjusting the strap member 20 of the circular headband 18 until proper elevation of the adjustable optical viewers 38 and 40 is obtained. The vertical positioning adjustment control knob 53 is illustrated in FIG. 2 along with a circular headband adjustment control knob 54. Tubes 56, 57, 58 and 59 are secured to the strap member 20. Tubes 56 and 57 attaches to the side of the adjustable optical viewer 38, and tubes 58 and 59 attach to the side of the adjustable optical viewer 40. The tubes 56 and 58 each deliver light and suction, and tubes 57 and 59 deliver irrigation fluids to each of the adjustable optical viewers 38 and 40 as provided for from an external source. Irrigation tubes 57 and 59 and the tubes 56 and 58, which carry suction, are removable for cleaning and can be disposable. Attachment receptors 60 and 62 are located in the front of the adjustable optical viewers 38 and 40 to provide for rapid connection of one end of tubes 65 and 67 internally, and each includes a visual fiber optic bundle 64, a light fiber optic bundle 66, and a suction tube 68. Irrigation tubes 69 and 71 reside in tubes 65 and 67, respectively. Tubes 65 and 67 comprise bundled fiber optics and tubing 16 between the head mounted viewing assembly 12 and the retractor 14.

The retractor 14 includes a flat paddle 70, a straight paddle neck 72 extending from the flat paddle 70, angled paddle neck 74, and a configured gripping handle 76 at the end of the angled paddle neck 74. Tubes 65 and 67 engage holes 78 and 80 in the lower portion of the angled paddle neck 74, and are secured by a bonding agent or other suitable means to the upper surface of the straight paddle neck 72. The tubes 65 and 67 extend along the length of the straight paddle neck 72 to pass through holes 82 and 84 in the flat paddle 70 to secure as previously described to the lower surface of the flat paddle 70 and terminate a finite distance from the end 86 of the flat paddle 70.

FIG. 2 illustrates a side view of the stereoscopic microsurgery system head mounted viewing assembly 12 as worn by a surgeon where all numerals correspond to those elements previously described. Illustrated in particular are the threaded adjustment knob 46 and lateral adjustment knob 50 on the threaded angle bracket 42 which are tightened against the adjustment plate 30 to provide adjustment of the adjustable optical viewer 38. The adjustable optical viewers 38 and 40 in the adjustment slot 36 can be adjusted fore or aft longitudinally, left or right laterally, and may also be pivoted about the horizontal axis of the threaded angle brackets 42 and 44. This provides x-y-z movement of the viewers as illustrated in FIG. 1.

Figure 3:
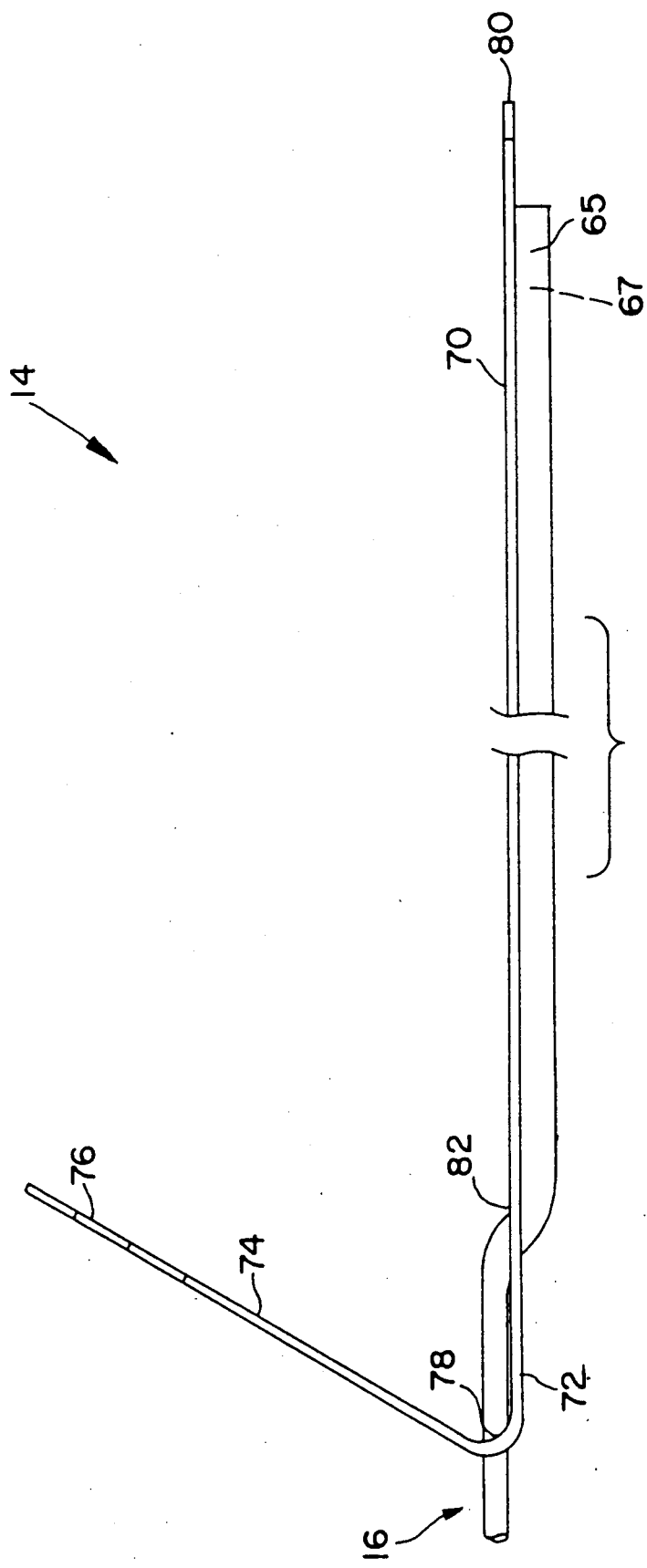
FIG. 3 illustrates a side view of the retractor.

FIG. 3 illustrates a side view of the retractor 14 where all numerals correspond to those elements previously described. The length and width of the flat paddle 70 are 20-25 cm and 3.5 to 4 cm, respectively, by way of example and for purposes of illustration only and not to be construed as limiting of the present invention. The length and width of the straight paddle neck 72 is 5 cm and 2 to 2.5 cm, respectively, and can be differently sized to accommodate particular types and styles of surgery. It is noted that the tubes 65 and 67 terminate prior to end 86 of the flat paddle 70, providing for sheltering of the ends of the tubes 65 and 67 from tissue so that a clear view of the surgical area can be viewed.

The mode of operation provides for depth of field viewing of an internal cavity in the human body by the stereoscopic viewing through the two fiber optic bundles. The system is used in the following procedures in Table 1.

TABLE 1

Anthroscopic
Laproscopic
Gastroscopy
Colonoscopy
Thorascopy
Anocoscopy
Esophagoscopy
Cystoscopy
Choudochoscopy The stereoscopic microsurgery viewing system particularly lends itself to use in implants of right or left breast prosthesis through the respective arm pit. In the past, surgeons have found it difficult to make an incision in the arm pit, and subsequently implant a breast enlargement prosthesis or breast reduction procedure. The present invention provides for not only stereoscopic viewing as to the placement of the breast prosthesis, but also depth of field viewing in the thoractic cavity.

The present invention is not limited to breast implants, but is intended for viewing of cavities within the human body in stereoscopic vision, including depth of field.

DESCRIPTION OF A FIRST ALTERNATIVE EMBODIMENT

Figure 4:
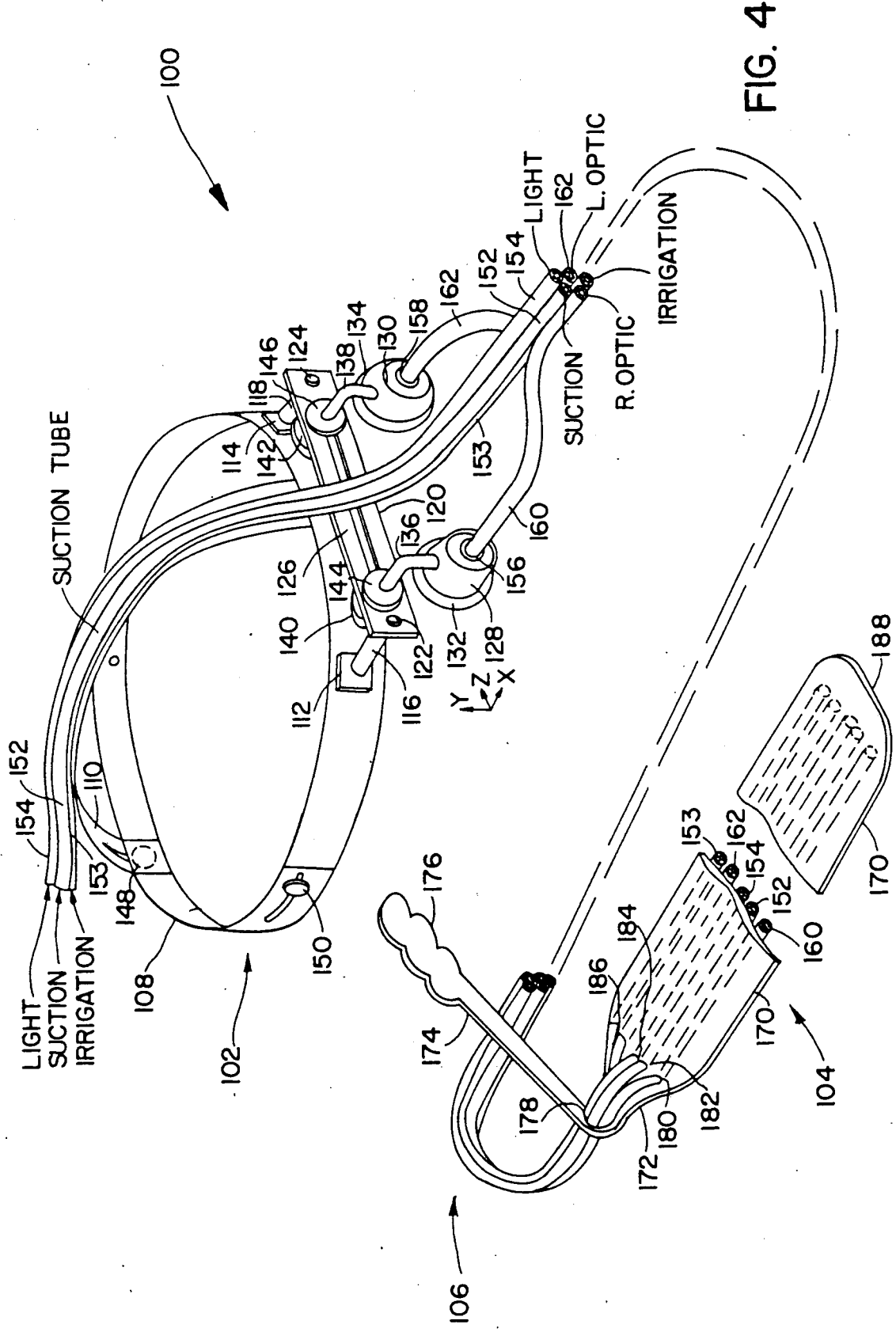
FIG. 4 illustrates a first alternative embodiment of a stereoscopic microsurgery system.

FIG. 4 illustrates a perspective view of an alternative embodiment 100 of a stereoscopic microsurgery system 100, similar in many aspects to that of the stereoscopic microsurgery system 10, including a head mounted viewing assembly 102, a retractor 104, and bundled fiber optic tubing 106 between the head mounted viewing assembly 102 and the retractor 104. The head mounted viewing assembly 102 includes a horizontally aligned adjustable circular headband 108, an adjustable vertically aligned strap member 110 extending from the front of the circular headband 108 to the rear of the circular headband 108, mounting blocks 112 and 114 secured to the circular headband 108, mounting posts 116 and 118 secured to and extending horizontally from the mounting blocks 112 and 114, respectively, a horizontally aligned adjustment plate 120 secured to the mounting posts 116 and 118 by machine screws 122 and 124, and an adjustment slot 126 extending horizontally through the adjustment plate 120. Also included in the head mounted viewing assembly 102 are adjustable optical viewers 128 and 130, rubber ring gaskets 132 and 134 about the aft edge of the adjustable optical viewers 128 and 130, respectively, and appropriate mounting hardware including threaded angled brackets 136 and 138 extending vertically from the adjustable optical viewers 128 and 130 and further extending horizontally through the adjustment slot 126. Threaded adjustment knobs 140 and 142 secure over the threaded angle brackets 136 and 138 in the adjustment slot 126 to locate and tighten against the adjustment plate 120. Opposing threaded adjustment knobs 144 and 146 also engage the threaded horizontal ends of the threaded angle brackets 136 and 138, and are tightened individually against the adjustment plate 120, forcing the threaded adjustment knobs 140 and 142 against the adjustment plate 120 to provide securement and independent lateral, longitudinal and pivotal adjustment of the adjustable optical viewers 128 and 130 so that a surgeon may properly space the optical viewers about his individual eyes. Vertical positioning of the adjustable optical viewers 128 and 130 is accomplished by adjusting the strap member 110 of the headband until proper elevation of the adjustable optical viewers 128 and 130 is obtained. The vertical positioning adjustment control knob 148, is similar to knob 53 as illustrated in FIG. 2, along with a circular headband positioning adjustment control knob 150. A suction tube 152, an irrigation tube 153 and a light bundle 154 and/or the light bundle secure to the strap member 110. The suction tube 152 and the irrigation tube 153 are removable and disposable for ease of sterilization. The fiber optic bundles and the paddle, based on replacement costs, can also be disposable. The tubes 152 and 154 deliver suction and light, respectively, to the end of the retractor 104 as provided for from an external source. Attachment receptors 156 and 158 are located in the front of the adjustable optical viewers 128 and 130 to provide for rapid connection of one end of fiber optic bundles 160 and 162. The suction or aspiration tube 152, the light tube 154, and the fiber optic tubes 160 and 162 comprise the bundled fiber optic tubing 106 between the head mounted viewing assembly 102 and the retractor 104.

The retractor 104 includes a flat paddle 170, a straight paddle neck 172 extending from the flat paddle 170, an angled paddle neck 174, and a configured gripping handle 176 at the end of the angled paddle neck 174. The bundled fiber optic tubing 106 engages hole 178 in the lower portion of the angled paddle neck 174, and are secured by a bonding agent or other suitable means to the upper surface of the straight paddle neck 172. Members of the bundled fiber optic tubing 106 extend along the length of the straight paddle neck 172 to pass through holes 180–186 in the flat paddle 170 and to secure as previously described to the lower surface of the flat paddle 170. The tubes 152 and 154, and optic bundles 160 and 162 terminate a finite distance from the end 188 of the flat paddle 170. The retractor 104 can include molded clips on the retractor for securing the fiber optic bundles or cables, the light cable and/or the suction or aspiration cable.

DESCRIPTION OF A SECOND ALTERNATIVE EMBODIMENT

FIG. 5 illustrates a perspective view of an alternative embodiment of a stereoscopic microsurgery system 200 including a head mounted viewing assembly 202, and a bundled fiber optic tubing 204 mounted on the head mounted viewing assembly 202. The head mounted viewing assembly 202 includes a horizontally aligned adjustable circular headband 206, an adjustable vertically aligned strap member 208 extending from the front of the circular headband 206 to the rear of the circular headband 206, mounting blocks 210 and 212 secured to the circular headband 206, mounting posts 214 and 216 secured to and extending horizontally from the mounting blocks 210 and 212, respectively, a horizontally aligned adjustment plate 218 secured to the mounting posts 214 and 216 by machine screws 219 and 220, and an adjustment slot 222 extending horizontally through the adjustment plate 218. Also included in the head mounted viewing assembly 202 are adjustable optical viewers 224 and 226, rubber ring gaskets 228 and 230 about the aft edge of the adjustable optical viewers 224 and 226, respectively, and appropriate mounting hardware including threaded angled brackets 232 and 234 extending vertically from the adjustable optical viewers 224 and 226 and further extending horizontally through the adjustment slot 222. Threaded adjustment knobs 236 and 238 secure over the threaded angle brackets 232 and 234 in the adjustment slot 222 to locate and tighten against the adjustment plate 218. Opposing threaded lateral adjustment knobs 240 and 242 also engage the threaded horizontal ends of the threaded angle brackets 232 and 234, and are tightened individually against the adjustment plate 218, forcing the threaded adjustment knobs 236 and 238 against the adjustment plate 218 to provide securement and independent lateral longitudinal and pivotal adjustment of the adjustable optical viewers 224 and 226 so that the surgeon can properly space the optical viewers about his individual eyes. Vertical positioning of the adjustable optical viewers 224 and 226 is accomplished by adjusting the strap member 208 of the circular headband 206 until proper elevation of the adjustable optical viewers 224 and 226 is obtained. The vertical positioning adjustment control knob 244 and a circular headband adjustment control knob 246 provide for adjustment of the headband 206. Tubes 248, 250, 252 and 254 are secured to the strap member 208. Tubes 248 and 250 attach to the side of the adjustable optical viewer 224, and tubes 252 and 254 attach to the side of the adjustable optical viewer 226. The tubes 248 and 252 each deliver light and suction, and tubes 250 and 254 deliver irrigation fluids to each of the adjustable optical viewers 224 and 226 as provided for from an external source. Irrigation tubes 250 and 254 and the tubes 248 and 252, each of which carries light and suction, are removable for cleaning and can be disposable. Attachment receptors 256 and 258 are located in the front of the adjustable optical viewers 224 and 226 to provide for rapid connection of one end of tubes 260 and 262 internally, and each receptor includes a visual fiber optic 264, a light fiber optic 266, and a suction tube 268. Irrigation tubes 270 and 272 also reside in tubes 260 and 262, respectively.

A tube 301 of the scope 302 and a opto-mechanical connector 304 are secured to tubes 260 and 262. The opto-mechanical connector 304 connects or converts light 266, suction 268 and optics 264 and irrigation 270 and 272 from each of the respective tubes 260 and 262 so that it can connect to and be used by the tube 301 of the scope 302. The tube 301 comprises a single light bundle 306, left and right optical bundles 308 and 309, a suction port 310 and an irrigation port 312, each of which connect to their appropriate source through the optomechanical connector 304. The tube 301 includes a quick connector 314 which snaps into the optomechanical connector 304. The scope 302 can be used as illustrated or can be attached to a retractor similar to the retractor 14 of FIG. 1.

FIG. 6 illustrates a cross-sectional view taken along line 6—6 of FIG. 5 where all numerals correspond to those elements previously described. Illustrated in particular are the single light bundle 306, left and right optic bundles 308 and 309, a suction port 310 and an irrigation port 312 integral to the tube 301. The tube 301 can be flexible or rigid and can have a thickness of 5 to 8 mm.

Figure 7:
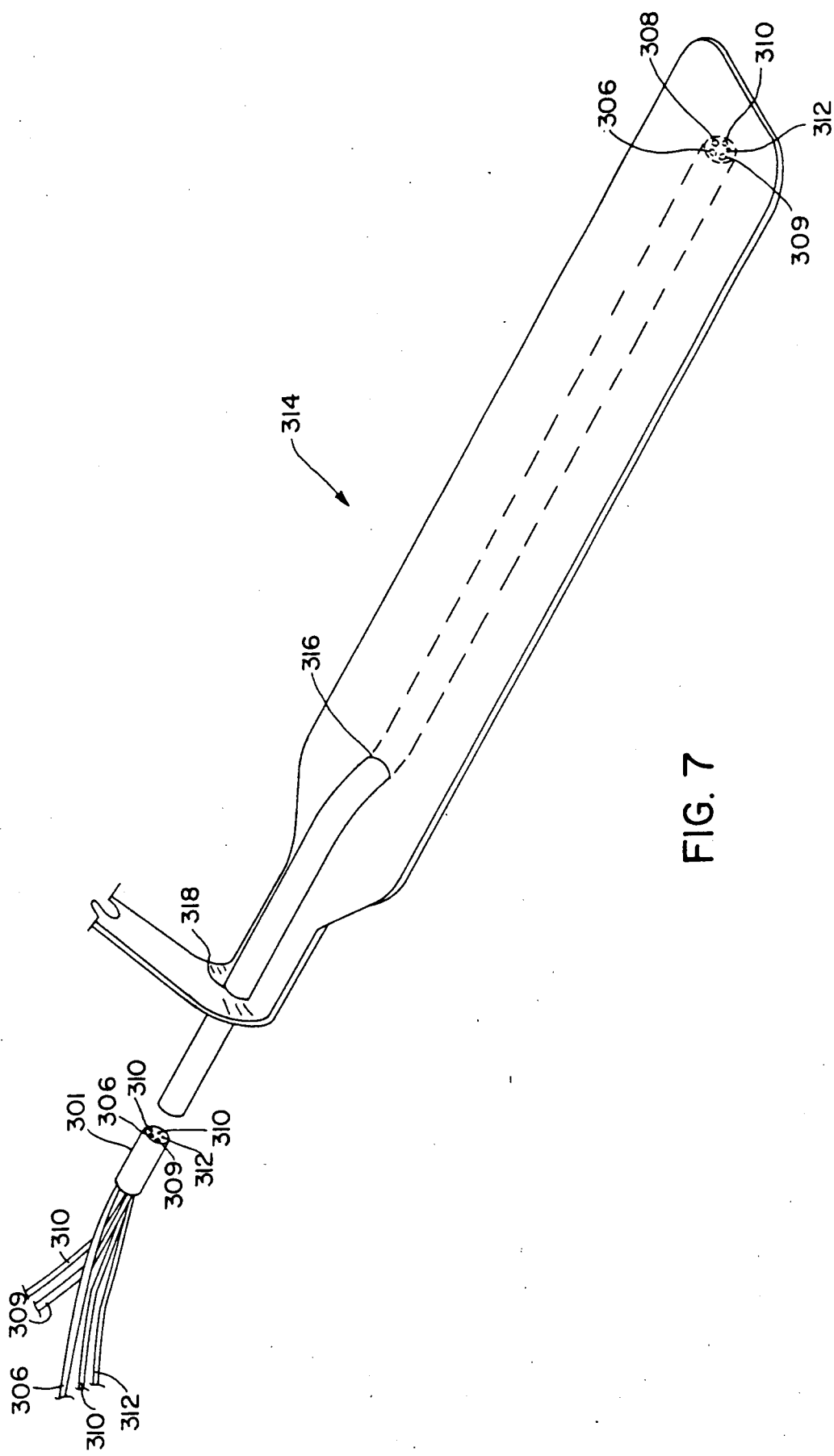
FIG. 7 illustrates the second alternative embodiment of the stereoscopic microsurgery system secured to a retractor.

FIG. 7 illustrates a perspective view of the second alternative embodiment of the tube 301 secured to a retractor 314 through holes 316 and 318 in the retractor 314. Only a single tube 301 is incorporated for stereoscopic viewing, light, irrigation and suction, thus allowing the use of a retractor which is of lesser width for use in difficult and small areas.

Various modifications can be made to the present invention without departing from the apparent scope hereof.

I claim:

1. A system for stereoscopic viewing of a microsurgery site comprising:
   a. a substantially flat planar paddle means with a handle;
   b. two fiber optic viewing bundles positioned about said paddle and extending to and about an end of said paddle means;
   c. adjustable optical viewing assemblies supported on a headband;
   d. said fiber optic bundles connected to said optical viewing assemblies; and,
   e. light means and suction/irrigation means positioned adjacent to each of said fiber optic viewing bundles.

2. System of claim 1 including a light tube connected to a light source, extending along said fiber optic bundles, and about said paddle.

3. System of claim 1 including a suction and/or aspiration tube extending from a suction or aspiration source, along said fiber optic bundles, and about said paddle.

4. System of claim 1 including optic means coupled to said paddle means end of said fiber optics.

5. System of claim 1 including optic means coupled to headband end of said fiber optics.

6. System of claim 1 wherein said viewing fiber optics are spaced a finite distance to provide stereoscopic viewing with depth of field.

7. Process for implanting a right or left breast prosthesis comprising the steps of:
   a. making an incision in an arm pit;
   b. inserting the stereoscopic viewing system of claim 1 through said incision and into the thoracic cavity; and,
   c. viewing placement of the breast implant prosthesis in said thoracic cavity.

* * * * *